(12) United States Patent
Barolet et al.

(10) Patent No.: US 8,226,634 B2
(45) Date of Patent: *Jul. 24, 2012

(54) METHOD FOR PROTECTING MAMMALIAN SKIN AGAINST UPCOMING PHOTODAMAGE

(75) Inventors: Daniel Barolet, Rosemére (CA); Annie Boucher, Montreal (CA)

(73) Assignee: Clinique Dr Daniel Barolet Inc., Town of Mount Royal (CA)

( * ) Notice: Subject to any disclaimer, the term of this patent is extended or adjusted under 35 U.S.C. 154(b) by 816 days.

This patent is subject to a terminal disclaimer.

(21) Appl. No.: 11/342,821

(22) Filed: Jan. 31, 2006

(65) Prior Publication Data

US 2006/0173512 A1 Aug. 3, 2006

Related U.S. Application Data

(60) Provisional application No. 60/648,415, filed on Feb. 1, 2005.

(51) Int. Cl.
*A61B 18/18* (2006.01)
(52) U.S. Cl. .............................. 606/9; 128/898; 607/88
(58) Field of Classification Search ........................ None
See application file for complete search history.

(56) References Cited

U.S. PATENT DOCUMENTS

| | | | | |
|---|---|---|---|---|
| 6,676,655 B2 * | 1/2004 | McDaniel | | 606/9 |
| 2002/0095143 A1 * | 7/2002 | Key | | 606/9 |
| 2003/0004556 A1 * | 1/2003 | McDaniel | | 607/88 |
| 2005/0045189 A1 * | 3/2005 | Jay | | 128/898 |
| 2005/0197681 A1 * | 9/2005 | Barolet et al. | | 607/86 |
| 2007/0231255 A1 * | 10/2007 | Barolet et al. | | 424/1.11 |

OTHER PUBLICATIONS

Menezes et al., Non-coherant near infrared radiation protects normal Human dermal fibroblasts from Ultraviolet Toxicity, J. Invest. Dermatol; Oct. 1998, pp. 629-633, vol. 11.*
Tsukahara K, et al. The effect of sunscreen . . . Biol Phanterior forearm Bull. Dec. 2005; pp: 2302-2307 vol. 728 No(12). Japan.
MoonYyung In et al Regulation effect of 2',4',7-trihydroxyisoflavone on the expression of matrix . . . Biol Phanterior forearm Bull. Nov. 2005; pp. 2173-2175 vol. 28 No.(11). Japan.
Xia Jiping et al UV-induced NF-kappaB activation and expression . . . Int J Mol Med. Nov. 2005; pp. 943-950; vol. 16. China.
Baumann Leslie. How to prevent photoaging? J Invest Dermatol. Oct. 2005;125: pp. xii-xiii. No (4) USA.
Stratigos AJ, et al The role of topical retinoids in the treatment of photoaging. Drugs. May 2005; pp. 1061-1072 vol. 65 No(8) Greece.
Han KH, et al Alteration of the TGF-beta/SMAD pathway in intrinsically and UV-induced skin aging. Mech Ageing Dev. May 2005; pp. 560-567; vol. 126 No.(5); Japan.

Fisher Gary J. The pathophysiology of photoaging of the skin. Cutis. Feb. 2005; pp. 5-8 vol. 75(2 Suppl); Michigan.
Moon Hi, Lee et al. The effect of tiarellic acid on the expressions of matrix . . . J Ethnophanterior forearmacol. Oct. 2005 April pp. 185-1189 vol. 8 No. 98 Japan.
Nishigori C, et al. Photoaging and oxidative stress. Exp Dermatol. 2003; pp. 18-21; vol. 12 Suppl 2; Denmark.
Maier T, Korting HC. Sunscreens—which and what for? Skin Phanterior forearmacol Physiol. Nov.-Dec. 2005; pp. 253-262; vol. 18 No.(6); Germany.
Loser K, et al. An important role of CD80/CD86-CTLA-4 signaling during photocarcinogenesis in mice. J Immunol. May 2005 ; pp. 5298-5305 vol. 174 No.(9); Germany.
Afaq F, et al. Photochemoprevention of ultraviolet B signaling and photocarcinogenesis. Mutat Res. Apr. 2005; pp. 153-173 vol. 571 No.(1-2); USA.
Agar N, et al. Melanogenesis: a photoprotective response to DNA damage? Mutat Res. Apr. 2005; pp. 121-132 vol. 571 No.(1-2); UK.
Melnikova Vo et al. Cellular and molecular events leading to the development of skin cancer. Mutat Res. Apr. 2005; pp. 91-106; vol. 571No.(1-2); USA.
Chen PH et al. Effects of arsenic and UVB on normal human cultured . . . Chem Res Toxicol; Feb. 2005; pp. 139-144; vol. 18No.(2); China.
Hussein Mahmoud R. Ultraviolet radiation and skin cancer: molecular mechanisms. J Cutan Pathol; Mar. 2005; pp. 191-205; vol. 32 No.(3); Denmark.
Wang Li-E et al. In vitro sensitivity to ultraviolet B light and skin cancer risk: a case-control analysis. J Natl Cancer Inst.; Dec. 2005; pp. 1822-1831; vol. 97 No.(24); USA.
Menezes S et al. Non-coherent near infrared radiation protects normal human dermal fibroblasts from solar ultraviolet toxicity. J Invest Dermatol; Oct. 1998; pp. 629-633; vol. 11.
Schieke S et al. Infrared-A radiation-induced matrix metalloproteinase 1 expression is mediated through extracellular . . . ; J Invest Dermatol.; Dec. 2002; pp. 1323-1329; vol. 119 No.
Kim Ho Hyeon et al. Augmentation of UV-induced skin wrinkling by infrared irradiation in hairless mice.; Elsevier Ireland; Nov. 2005; pp. 1-8; vol. 126 No.(11); Japan.
Schieke Stefan M. et al. Cutaneous effects of infrared radiation: from clinical observations . . . ; Photodermatol Photoimmunol Photomed.; Oct. 2003; pp. 228-234; vol. 19 No.(5); Germa.
Halper J et al. In vitro culture decreases the expression of TGF(beta), Hsp47 and type . . . ; J Musculoskelet Neuronal Interact.; Mar. 2005; pp. 53-63; vol. 5 No.(1); USA.
Barolet Daniel et al. In vivo human dermal collagen production following LED-based therapy . . . ; Laser Medicine and Surgery; Mar. 30-Apr. 3, 2005. Poster session (259) Canada.

(Continued)

*Primary Examiner* — Ernst Arnold

(57) ABSTRACT

A method for protecting mammalian skin against photodamage caused by an exposure to a damaging radiation. The method includes irradiating the mammalian skin before the exposure to the damaging radiation with a protective radiation, the protective radiation including radiation having a wavelength larger than the wavelength of the damaging radiation, the protective radiation being irradiated onto the mammalian skin under conditions suitable for reducing photodamage to the mammalian skin caused by the damaging radiation.

13 Claims, 1 Drawing Sheet

OTHER PUBLICATIONS

Marionnet Claire et al. Modulation of gene expression induced in human epidermis . . . ; J Invest Dermatol.; Dec. 2003; pp. 1447-1458; vol. 121 No.(6); France.

Morliere P et al. [Ultraviolet A radiation and the skin. Implications of activated forms of oxygen . . . ]; Pathol Biol (Paris).; Feb. 1992; pp. 160-168; vol. 40 No.(2); France.

Frank Sandra et al. Infrared radiation affects the mitochondrial pathway of apoptosis in human fibroblasts. J Invest Dermatol.; Nov. 2004; pp. 823-831; vol. 123 No. (5); France.

Djavaheri-Mergny M. et al. NF-kappaB activation prevents apoptotic oxidative stress via an increase of both . . . ; FEBS Letter; Dec. 3, 2004; pp. 111-115; vol. 578 No.(1-2); France.

\* cited by examiner

| Control arm | |
|---|---|
| Untreated control 14a | |
| Control sunscreen SPF 15 (MED 1): *Positive control* 14b | |
| Tested MED number 1 14c | |
| Tested MED number 2 14d | |
| Tested MED number 3 14e | |
| Tested MED number 4 14f | |

| Tested arm | |
|---|---|
| Control sunscreen SPF 15 (MED 1) 16a | |
| LumiPhase-R used alone as control 16b | |
| 1 MED: 16c | |
| 2 MED: 16d | |
| 3 MED: 16e | |
| 4 MED: 16f | |

10

12

METHOD FOR PROTECTING MAMMALIAN SKIN AGAINST UPCOMING PHOTODAMAGE

This application claims priority from U.S. Provisional Patent Application Ser. No. 60/648,415 filed Feb. 1, 2005.

FIELD OF THE INVENTION

The present invention relates to the prevention of radiation damage. More specifically, the present invention is concerned with a method for protecting mammalian skin against upcoming photodamage.

BACKGROUND OF THE INVENTION

Encouraging photoprotection is a leading preventative health strategy used by physicians involved in skin care. Although sun avoidance is most desirable, outdoor occupations and lifestyles make total avoidance impossible for many individuals.

Solar UV (Ultraviolet) insults often damage cells, leading to premature photoaging (1-8) and carcinogenesis (9-17). Currently, there are 2 main method used to protect mammalian skin against UV damage.

In the first method, a composition of matter that absorbs ultraviolet radiation, also called a sunscreen, is applied to the skin of a subject. Therefore, only a relatively small quantity of UV radiation reaches the skin. However, the substances contained in the composition of matter are degraded by the UV radiation and other environmental factors. Accordingly, the protection provided by a single application of the composition of matter lasts only for a relatively short amount of time, and there is a need to frequently reapply the composition of matter on the skin of the subject. Also, some authors suggest that at least some of the substances used to protect against UV damage might themselves be carcinogenic.

Furthermore, the UV absorbing substances are often mixed with hydrophobic substances to better penetrate the skin. They therefore produce an often undesirable "oily" texture onto the skin. This disadvantage may be strong enough that some subjects refuse to use the composition of matters.

UV radiation (UVR) that reaches the Earth's surface can be divided into UV-B (290-320 nm) and UV-A (320-400 nm). UV-A can be further subdivided into UV-A I, or far UV-A (340-400 nm), and UV-A II, or near UV-A (320-340 nm). The sun protection factor (SPF) is defined as the dose of UVR required to produce 1 minimal erythema dose (MED) on protected skin after the application of 2 mg/cm2 of product divided by the UVR required to produce 1 MED on unprotected skin. A water-resistant product maintains the SPF level after 40 minutes of water immersion, whereas a very water-resistant (also known as waterproof) product maintains the SPF level after 80 minutes of water immersion. A broad-spectrum or full-spectrum sunscreen provides both UV-B and UV-A protection, ideally through the entire UV-A I and UV-A II range. Erythema, the key measurement in the SPF assay, is a relatively crude biologic endpoint. A comparison of a SPF 15 sunscreen versus a SPF 30 sunscreen showed subclinical damage (sunburn cell formation) in the former without visible erythema. The SPF 30 product provided significantly greater protection. Other forms of subclinical damage may occur with a SPF 15 formulation.

Although UV-A protection may be less than desirable with all sunscreen products, the UV-A protection is better with a higher SPF, particularly in the UV-A II (320-340 nm) or shorter UV-A range. Although sunscreens provide excellent UV-B protection, they lack in UV-A protection, particularly UV-A I. No consensus exists about the best method for measuring UV-A protection. A variety of methods have been proposed. In vivo methods have been developed on the basis of direct UV-A erythema, persistent pigment darkening, and photosensitization with psoralens. At best, each method has its limitations and indications for a particular clinical situation or skin type. An in vitro method relying on transmittance through a thin substrate, such as thin film, may be more practical and is currently used in Europe. If protection from UVR into the UV-A I range is desired, the formula should contain either avobenzone or an inorganic particulate sunscreen as an active ingredient.

Sunscreens alone may also provide insufficient protection from UVR. Sunscreens function best to prevent sunburn from UV-B radiation. They provide more limited protection from UV-A radiation. Sole dependence on sunscreens can have the unwanted effect of increasing outdoor exposure times, particularly in those individuals who burn easily and tan poorly. Sun avoidance remains the most desirable form of sun protection.

Typically, sunscreen should be applied 15-30 minutes prior to sun exposure to allow sufficient time for a protective film to develop. Sunscreen should be reapplied after prolonged swimming or vigorous activity. Sunscreen needs to be applied in relatively large quantities. As much as 1 oz may be needed to cover the entire body. Particular attention needs to be paid to the back of the neck, the ears, and the areas of the scalp with thin hair. All these limitations often result in improper use of sunscreens, and consequently to sub-optimal protection from damaging radiations.

In the second method, the skin is irradiated with UV radiation under controlled conditions to stimulate the natural production of UV absorbing skin pigments. A disadvantage of this method is that while some damage is prevented when a solar UV exposition is performed onto the skin thereafter, the preventive treatment still causes some potential UV skin damage.

The present document makes reference to a number of documents, the contents of which is hereby incorporated by reference in their entirety.

Against this background, there exists a need in the industry to provide novel methods for protecting mammalian skin against upcoming photodamage.

An object of the present invention is therefore to provide an improved method for protecting mammalian skin against upcoming photodamage.

SUMMARY OF THE INVENTION

In a first broad aspect, the invention provides a method for protecting mammalian skin against photodamage caused by an exposure to a damaging radiation. The method includes irradiating the mammalian skin before the exposure to the damaging radiation with a protective radiation, the protective radiation including radiation having a wavelength larger than the wavelength of the damaging radiation, the protective radiation being irradiated onto the mammalian skin under conditions suitable for reducing photodamage to the mammalian skin caused by the damaging radiation.

In a specific embodiment of the invention, the damaging radiation includes UV radiation and the protective radiation includes radiation having a wavelength of between 400 and 950 nm. In other embodiments of the invention, the damaging radiation includes visible light, infrared radiation, or both.

In some embodiments of the invention, the mammalian skin is irradiated over at least two treatments, each treatment including a plurality of radiation pulse trains.

For example, in some embodiment there is a photoprotection against UV insults and upcoming photodamage of mammalian skin. The prevention of actinic and UV damages is performable with non-thermal LED treatment prior to sun/UV exposure and has a potential to reduce UVB-induced erythema reaction in a dose related manner. Clinical work confirms this SPF-like novel photoprotection between 8 and 15, but that could reach a protective-like factor of 25. In a non-limiting specific example, non-thermal, non-coherent 660 nm LED (having a bandwidth of from about 10 nm to about 50 nm) light therapy is a prophylaxic modality against upcoming UV/sun insults.

A clinical protocol involving the determination of the minimal erythema dose (MED) with or without non-thermal non-coherent close/near IR light exposure prior to UV exposure was performed to investigate actinic UV damage prophylaxis by non-thermal LED pulsed 660 nm (close to/near infrared radiation) light.

Advantageously, the claimed method reduces the risk of sunburn during any sun exposure, helps the skin to develop a faster protection to upcoming UV rays and protects the skin and prevents at least in part photodamage/photoaging (premature aging). For example, the claimed method is usable to protect against UV damage while simply practicing outdoor activities, vacationing south/north, going to tanning salon or when undergoing PUVA or any medical UV treatments for a skin disease such as psoriasis, eczema, among others. Such photoprotection is also advantageous when repeated applications of a topical sun protection are unachievable. In addition, the claimed photoprotection method would not be affected by water, perspiration, etc. It would also allow for topical creams, insect repellant, etc, to be used concomitantly, without interference. There is also no risk of contact dermatitis such as PABA and/or benzofenones typical allergic reactions encountered with sunscreen.

UV protection for patients with actinic hypersensitivity (PLE: polymorphous light eruption, hydroa estivale, etc.), sun sensitive disease (i.e. SLE: systemic lupus erythematosis, PCT: porphyria cutanea tarda) or under photosensitizing drugs, either topical or systemic, may also be provided. Accordingly, in some embodiments of the invention, the damaging radiation includes radiation intended to treat a medical condition, the protective radiation reducing side effects of the damaging radiations while allowing the treatment of the medical condition to occur.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

Embodiments of the present invention will now be disclosed, by way of example, in reference to the following Figure:

FIG. 1, in a schematic view, illustrates a pattern of mammalian skin irradiation with protective radiation performed in experiments exemplifying an embodiment of the present invention.

DETAILED DESCRIPTION

A previous in vitro study conducted by Menezes and collaborators in 1998 described the induction of a strong cellular defense against solar UV cytotoxicity after a single non-coherent near infrared ((primary-culture human fibroblasts were irradiated (400-2000 nm, wavelengths shorter than 700 nm were removed by a Schott RG715 filter, 45mW/cm2 delivered for 30 minutes; total fluence 810 kJ/m2)) radiation, in the absence of rising temperature (18). A single irradiation was performed without temperature increase, providing human skin fibroblasts a 24 hours protection against solar UV radiation.

In the Menezes study, fibroblasts were irradiated with radiation involving infrared-A (760-1440 nm) and part of the infrared-B spectrum. While it has been reported that IR-A can penetrate the epidermal and dermal layers and reach the subcutaneous tissue without increasing the skin temperature significantly, IR-B is absorbed mostly in the epidermal layers, increasing skin temperature significantly (19). Skin temperatures increase causes decrease in collagen integrity and production, as described in Halper, 2005. Moreover, Recent studies have pointed out possible unrecognized properties of infrared-A, in association with photoaging. In fact, infrared-A irradiation of hairless mice and human dermal fibroblasts respectively lead to significant increase in MMP-13 and MMP-1, both collagenases, clearly associated with photodamage/aging/photoaging (19, 20, 21). Further, since it has been clearly shown that the in vitro work does not necessarily correlate with the in vivo work, we choose to investigate this phenomenon in vivo (human) using a well established MED (minimal erythema method.

Work performed in our laboratory identified relatively high power, non thermal non ablative 805 nm radiation as providing less dermal type I procollagen production in human reconstructed skin (in vitro model of human epidermis and dermis) of woman aged 38, 42 and 64 year-old, when compared to 660 nm, underlying potential parameter's importance in achieving such photoprotection. At non-thermal, pulsed 660 nm, when 11 treatments (total fluence of 4J) were delivered over one-month period, three times a week, MMP-1 (matrix metalloproteinase-1) production showed an inverse pattern of secretion when compared to cyclical increase of type I procollagen production These results are presented in US Patent Application Publication Number US20050197681A1 of Barolet et al., published Sep. 8, 2005, the contents of which is hereby incorporated by reference. Infrared-A radiation was found to induce matrix metalloproteinase-1 (MMP-1) at 760-1400 nm (21). Moreover, a close to IR wavelength such as 660 nm ensured a non-thermal treatment while non coherent IR reaching deeper in the dermis layer may increase collagen temperature (19). In Harper et al. (2005), type I procollagen production is reduced at 43° C. when compared to 37° C. (22).

The results presented hereinbelow show that surprisingly, non-thermal, non-coherent close to/near infrared (IR) multiple irradiations at 660 nm, under specific treatment parameters, stimulates skin resistance to UV damage, offering a protection against possible upcoming photodamage by damaging radiation in the form of UV radiation. It is hypothesized that at 660 nm, LED (light emitting diode) skin therapy promotes the production of dermal collagen secreted de novo, providing an improved overall appearance: reduction in wrinkle depth, pore size and redness (23). Non-thermal non-coherent close to/near IR light could increase dermal fibroblast procollagen secretion while reducing or stabilizing metalloproteinases (MMP) or collagenase production, and also triggering molecular pathways that remains to be established. However, this hypothesis should not be used to limit the scope of the appended claims that do not specifically claim this mechanism.

Indeed, among other effects, photoprotective effects of non-thermal, non-coherent close to/near infrared (IR) light could be very useful for patients as a prophylaxis against possible UV damage (both UVA and UVB), maintaining/promoting collagen production in the dermis and counter acting collagenase (collagen degrading enzyme) release associated to sun exposure and photoaging. For instance, a person vacationing during the winter may wish skin protection from intense sun before departing. Photoprotective effect could act as a relatively long-lasting SPF (Sun Protection Factor)-like protection factor, for example lasting up to 4 weeks after treatments have stopped, and not being affected by water or perspiration or any physical or environmental factor. Patients with actinic hypersensitivity (PLE=polymorphous light eruption, hydroa estivale, etc.), or taking photosensitizing drugs may also benefit from the claimed method.

More specifically, and still non-limitingly, the mechanisms involved in this photoprophylaxis could target the ATP cycle as well as mitosis and chaperones. However it was observed that specific stress proteins such as, heat shock (Hsp27 preventing apoptosome assembly, GADD45, Bax, SAS, MRP8, MRP14 and granulocyte chemotactic Protein-2 can be overexpressed by solar radiation (24). Involvement of activated oxygen species in the responses of skin to solar UV radiations does outline the concept of photooxidative stress (25). In vitro testing suggests mitochondria as a primary target of IR radiation (25). It was shown that IR pre-irradiation inhibited UV-B activation of Caspase-9 and -3, leading to the study of early events of the mitochondrial apoptotic pathway after irradiation (26). In a study published in 2004, IR irradiation led to a partial release of cytochrome c and Smac/Diablo but not apoptosis-inducing factor (AIF). A slight but transient decrease in the mitochondrial membrane potential (Deltapsim) by the insertion of Bax into the mitochondrial wall was also observed, despite a lack of caspase-9 and -3 activation. Moreover, the balance between pro-apoptotic (i.e., Bax) and anti-apoptotic (i.e., Bcl-2 or Bcl-xL) proteins, which was rather pro-apoptotic after IR exposure, became anti-apoptotic 24 h later, suggesting a protective effect. In addition, UV-A was shown to reduce nuclear factor-KappaB DNA binding activity in vitro, p50 and p65 protein subunits in human keratinocytes (27). Cell-cell communication between keratinocytes and dermal fibroblasts could also be involved in these complex photoprotection pathways.

For the purpose of this document, the following definitions are used. The MED is the quantity of erythema-effective energy required to produce the first perceptible, unambiguous redness reaction with clearly defined borders at 22 to 24 hours post exposure. The SPF value of the tested non-thermal 660 nm light would be calculated from the dose of UV radiation required to produce the MED of the 'protected' skin (660 nm pre-treatment) and from the dose of UV radiation required to produce the MED of the unprotected skin (control site) as follows: SPF value=the ratio of erythema effective exposure (Joules per square meter) (MED (protected skin: control sunscreen or 660 nm photoprotection (LumiPhase-R) treatment)) to the erythema effective exposure (Joules per square meter) (MED (unprotected skin)).

In some embodiments, the claimed invention includes a method for protecting mammalian skin against photodamage caused by an exposure to a damaging radiation, the method including irradiating the mammalian skin before the exposure to the damaging radiation with a protective radiation. The protective radiation includes radiation having a wavelength larger than the wavelength of the damaging radiation. The protective radiation is irradiated onto the mammalian skin under conditions suitable for reducing photodamage to the mammalian skin caused by the damaging radiation. For example, the mammalian skin is human mammalian skin.

Evolutionary adaptation to light and mechanisms of action of light on living mammalian cells.

To understand the manifestation of evolutionary adaptation to natural light, we shall consider some fundamental photochemical properties of organic molecules. But at first we shall give the following statement. All molecules, of which living organism consists, can be divided into two groups. 1) The molecules, which do not practically absorb light in the field of radiation of the sun at ground surface. Also it is necessary to take into account optical and photochemical properties of surface layers of skin. These molecules can only play a role of substrates in any photosensitized processes (examples—albumin, trypsin). 2) The molecules, capable to absorb light of the sun. As a consequence of evolutionary adaptation they have such properties, which provide animal with normal ability to live on light. Organic molecules of the second group in lower excited states do not change direction (character, sort) of their reactionary ability in comparison with their ground state. At absorption of a quantum of light by a molecule, the rate constants of chemical reactions only increase. Therefore, any light with low intensity does not introduce new biochemical responses to an organism, but only accelerates part of them, i.e. light accelerates biochemical responses already existing in an organism. As a result, the instant balance of the network of biochemical processes shifts.

Natural (solar, white) light, to which organism and its tissues are evolutionary adapted, accelerates such set of bioprocesses, which does not disturb total balance of biochemical responses, since the protective responses of an organism immediately (or with delay) eliminate abnormalities (except in acute injuries such as a sunburn). As a result, the biochemical state of an organism remains practically unchanged. It constitutes photochemical aspect of adaptation of an organism to natural light. Specially configured light, like LEDs down to relatively narrowband/monochromatic wavelengths, to which living organisms had not been adapted during evolution, accelerates rather narrow sets of biochemical responses, which alter the natural balance of biochemical processes. In other words, the natural protective ability and responses of an organism are not sufficient to resist to narrowband or monochromatic light. Therefore, narrowband/monochromatic light may trigger specific gene expression (either upregulation or downregulation) leading to an increase state of resistance (sun-resistant phenotype) to the skin against upcoming UV/sun insults (especially acute photodamage).

The claimed invention is a novel method that activates protective mechanisms in tissue for protecting against a damaging radiation having higher energy per photon using a preventive radiation having lower energy per photon. The use of lower energy photon has a potential to provide protection against damages caused by the higher energy photons while reducing the likely damage caused to the tissue that would occur if radiation similar to the damaging radiation were used to activate protective mechanisms in the tissue.

For example, the damaging radiation includes UV radiation and the protective radiation includes radiation having a wavelength has a wavelength of from about 400 nanometers to about 950 nanometers. The protective radiation defines at least one pulse train including a plurality of radiation pulses. The pulses each have a duration of from about 100 microseconds to about 5 milliseconds, the pulses being separated from each other by an inter-pulse interval, the inter-pulse interval being of from about 1 microsecond to about 1 milliseconds. The power density of each pulse in the tissue is of from about 20 mw/cm2 to about 100 mW/cm2. All the parameters describing the radiation are either adjusted independently from each other or adjusted in combinations causing synergetic effects within the tissue.

The exact values for the various pulse parameters depend on the effect that is sought. Examples of more specific values and of effects that are sought are given hereinbelow.

In one of these examples, the pulses each have a duration of from about 250 microsecond to about 1 millisecond. In a very specific example of implementation, the pulses each have a duration of about 500 microseconds.

In another of these examples, the inter-pulse interval is of from about 100 microseconds to about 0.5 milliseconds. In a very specific example of implementation, the inter-pulse is about 150 microseconds.

While the pulse duration and the inter-pulse intervals may be considered separately from each other, it is also within the scope of the invention to consider synergetic effects related to these two parameters.

For example, the ratio of the pulse duration divided by the pulse interval takes any suitable value. In a specific example of implementation, the ratio of the pulse duration divided by the pulse interval is within the interval of from about 0.1 to about 10. In a very specific example of implementation, the ratio of the pulse duration divided by the pulse interval is within the interval of from about 0.5 to about 2.

A specific example of a suitable power density of each pulse in the tissue is a power density contained within the interval of from about 20 mW/cm$^2$ to about 100 mW/cm$^2$. In some embodiments of the invention, the power density is about 20 mW/cm$^2$. A total fluence of from about 2 to 10 J/cm$^2$ or 2 to 6 J/cm$^2$, depending on the other parameters of the protective radiation is very likely to produce desired effects, with a fluence of 4J/cm2 having been shown to produce protection against the damaging radiation.

In a specific example of implementation, the method includes irradiating the tissue with radiation defining a plurality of pulse trains, each pulse train including a plurality of radiation pulses. For example, each pulse train includes from 2 to 100 pulses. The pulse trains are separated by inter-train time intervals wherein no pulses are produced, the inter-train intervals lasting from about 500 microseconds to about 2.25 milliseconds.

In some embodiments, the mammalian skin is cooled so as to maintain the mammalian skin at a temperature below a predetermined overheating temperature. For example, the overeating temperature is about 5° C. above a maximal non-pathological in-vivo tissue temperature.

The term pulse is to be broadly interpreted. For example, the pulses need not be of a substantially uniform power density with a substantially total absence of power density within the inter-pulse intervals, even if such pulses are an example of pulses suitable for use in some embodiments of the invention.

Indeed, each pulse may present a time evolution leading to pulses having any suitable time evolution. Also, during the inter-pulse interval, the power density is substantially smaller than a power density within each pulse, but not necessarily zero. Examples of such power density during the inter-pulse intervals are given hereinbelow.

In a non-limiting specific example of implementation, the inter-train intervals last from one of about 500 microseconds to about 2.25 and about 500 microseconds to about 1 millisecond and each pulse train includes from 3 to 10 pulses. The ratio of the inter-train interval to the inter-pulse interval is of from about 2 to about 10, and in a very specific example of implementation, the ratio of the inter-train interval to the inter-pulse interval is of about 3.

It is believed the application of pulse trains, as opposed to continuous light, leads to an enhance effect by the radiation on the skin for reasons similar to reasons stated in the above-mentioned Patent Application Publication of Barolet et al.

In some embodiments of the invention, a tissue is irradiated over at least two treatments, for example from 2 to about 10 treatments, and the treatments are provided with an inter-treatment time interval therebetween. Further, within each treatment, the power density temporal profile during the treatment defines a plurality of pulse trains, each pulse train including a plurality of radiation pulses having a predetermined pulse duration and being separated from each other by an inter-pulse time interval. The pulse trains are separated from each other by an inter-train time interval, the inter-train interval being substantially larger than the inter-pulse interval and the irradiation is performed under conditions suitable for substantially reducing photodamage to the mammalian skin caused by the damaging radiation. For example, the inter-treatment time interval is from about 12 hours to about 4 days, and more specifically, the inter-treatment time interval may be about 24 hours.

The protection provided by the claimed method is believed to be effective right after the last photoprotection treatment and to last from about 2 days to about to 4 weeks, depending on the exact parameters used during the irradiation with the protective radiation. For example, from about 2 to about 10 treatments.

More details concerning the operation and structure of the apparatus used to perform the treatments are found in the above-mentioned US Patent Application Publication Number US20050197681A1 of Barolet et al., published on Sep. 8, 2005.

It is believed that the mechanisms responsible for skin treatment to repair existing damages could involve similar mechanisms responsible for the claimed protective effect. Accordingly, while the results presented in this document have been obtained using only a few specific values of the parameters, the results that were obtained and that are presented hereinbelow suggest that the ranges of parameters discussed hereinabove are inferable from these results.

EXAMPLE

Methods Description:

Two healthy female participants (32 and 47 year old, phototype II) were involved in this study protocol. Participant's medical history and health condition was reviewed by a medical doctor: the subject had to meet the study requirements and protocol's exigencies, as detailed hereinbelow. The general health of the individual was ascertained, as well as the individual's skin type (phototype I or II), whether the individual is taking medication (topical or systemic) that is known to produce abnormal sunlight responses, and whether the individual is subject to any abnormal responses to sunlight, such as a phototoxic or photoallergic response. A physical examination determined the presence of sunburn, suntan, scars, active dermal lesions, and uneven skin tones on the areas of the anterior forearm to be tested. The presence of nevi, blemishes, or moles was acceptable, if in the physician's judgment they were not interfering with the study results. Experiments were performed on the anterior forearm.

Inclusion Criteria:

Adult healthy subjects

Area to be treated: the anterior forearm

Fair-skin subjects with skin types I and II according with the following guidelines:

Skin Type and Sunburn and Tanning History (Based on first 30 to 45 minutes sun exposure after a winter season of no sun exposure.)
I—Always burns easily; never tans (sensitive).
II—Always burns easily; tans minimally (sensitive).
III—Burns moderately; tans gradually (light brown) (normal).
IV—Burns minimally; always tans well (moderate brown) (normal).
V—Rarely burns; tans profusely (dark brown) (insensitive).
VI—Never burns; deeply pigmented (insensitive).

Exclusion Criteria:

Subject under 18 years of age

Current use of the following medications: (Prednisone), anticoagulant therapy, drugs known to cause photo-sensitivity reactions. In addition, during 12 months preceding the study, subjects are required not to take Accutane (isotretinoin).

Use of corticosteroids on the treated area within 2 weeks of first treatment.

Use of topical tretinoin for at least 1 month prior to enrolment.

Tanned skin around or on the area to be treated: the back.

Previous laser of medicated treatment at the treatment site (to be studied) and for the duration of the study.

Known diseases:
Skin: vitiligo, psoriasis, severe eczema, poor skin healing.
Chronic or acute: active infection, immunosuppression, coagulation problem, peripheral arterial disease, hematologic abnormalities, vasculitis, and previous history of epilepsy.

Pregnancy.

Alcohol or drug abuse before and during the study.

Participation in another study which may interfere with this trail results during 4 weeks preceding this study.

Test site areas were selected on both anterior forearms. One anterior forearm was used for baseline MED determination and control, 24 hours before the MED determination with previous protective irradiation. The control anterior forearm was used to monitor test parameters. Control and test area were treated according to the experiment grids found in FIG. 1.

On the control arm, a control test area 10 included substantially contiguous regions of skin designated as an untreated control area 14a, a positive control area 14b for applying a sunscreen thereon and 4 MED-determined areas 14c-14f. On the tested arm, i.e. the arm that was irradiated with the protective radiation, a test area 12 included substantially contiguous regions of skin that were designated a control area 16a for applying a sunscreen thereon, a control area 16b and 4 MED-testing areas 16c-14f.

The first 660 nm photoprotection (LumiPhase-R) (OPUSMED, inc. Montreal, Canada) irradiation treatment was performed on the day pre-treatment evaluation was completed. The 660 nm protective radiation (LumiPhase-R) is a pulsed 660 nm Light Emitting Diode (LED) light. It is non-thermal and non ablative light that is emitted with a proprietary sequential pulsing pulse. Its treatment head delivers 50 mW/cm2.

Description of parameters tested on each study participants is found in Table 1. Each participant received a predetermined number of 660 nm photoprotection (LumiPhase-R) treatments, on the test anterior forearm, prior to UV-B irradiation. Minimal erythema dose (MED) determination performed 24 hours prior to MED testing achieved the last 660 nm photoprotection (LumiPhase-R) treatment day. Photoprotection (LumiPhase-R) treatment anterior forearm was determined at random by like flipping a coin, no 660 nm photoprotection (LumiPhase-R) treatment was performed on the control anterior forearm. Selected test areas were then treated with the LumiPhase-R (660 nm, sequential pulsing mode), at a power density of 50 mW/cm2, for a total of 4 J (2m40 s). After respectively three or ten treatments, UV-B radiation were delivered on both the control anterior forearm and test side to respectively determine the subject's MED and proceed with MED testing.

The following parameters were used for each treatment:
Pulsewidth (time on) (μsec) 500:
Inter-Pulse Interval (time off) (μsec) 150
Number of Pulses per Pulse Train (number of pulse) 4
Inter-Train Interval (μsec) 1550
Irradiance (mW/cm$^2$) 50
Total Treatment Time (sec) 160

The UV-B lamp (Cooper Hewitt PH-36 Psoriasis Phototherapy Lamp, KBD, Inc. Kentucky, USA) was used for MED experiments. UV protective eyewear was worn when the lamp is operating. Since different skin types require different times of exposure, and MED for average type skin (Type II) is approximately three minutes at a distance of four inches from the light source, MED was precisely evaluated determined for each study participant. After UV-B exposure, reddening appeared and pictures were taken. UV-B radiation was delivered (UV-B and UV-A output averages: 35% UV-B and 65% UV-A), by a lamp emitting 800 W of continuous wave power. Tested UV-B doses reaching the skin reached from 50 to 200 kJ/cm2.

Application of positive control sunscreen (SPF 15):

A control SPF 15 sunscreen was also used as positive control. To ensure standardized reporting and to define a product's SPF-like value, the application of the product is expressed on a weight basis per unit area which establishes a standard film. Control sunscreen application was about two milligrams per square centimeter.

Minimum erythema dose (MED) was assessed for each patient. Baseline UV-B MED was read 24 hours after the MED test. Pictures were taken and redness analyzed, compared to control area in term of % improvement (% less redness after treatment). Digital pictures were taken prior UV exposure, right after UV exposure (STAT), as well as each hour following the experiment to monitor redness progression for the five hours post UV-B irradiation.

Immediately after each MED treatment, the subject was asked to rate the pain on scale of 1 to 10. Clinical evaluation of purpura, edema, erythema, hyperpigmentation, hypopigmentation, blistering and scaring were assessed for each treatment and control window, using the following scale: 0=absence, 1=mild, 2=moderate, 3=severe. Finally, the subject was instructed on post-treatment care of the treatment area including the use of sun avoidance.

Determination of MED of the Unprotected Skin:

Doses selected were a geometric series represented by 1 n, 2n, 3n, 4n, wherein each exposure time interval was 100 percent greater than the previous time to maintain the same relative uncertainty (expressed as a constant percentage), independent of the subject's sensitivity to UV radiation, regardless of whether the subject has a high or low MED.

The MED of unprotected skin was determined the day prior to testing a product. This MED was later used in the determination of the series of UV radiation exposures to be administered to the protected site in subsequent testing. The MED were determined again on the same day as the standard and used in calculating the SPF.

Determination of Individual SPF-Like Value:

660 nm photoprotection (LumiPhase-R) treatments were performed prior to UV radiation to assess non-thermal 660 nm light photoprophylactic effects.

Testing depended upon determining the smallest dose of energy that produces redness reaching the borders of the exposure site at 22 to 24 hours post-exposure for each series of exposures. To determine the MED, somewhat more intense erythemas were produced. The goal was to have some exposures that produced absolutely no effect, and of those exposures that produced an effect, the maximal exposure should be no more than twice the total energy of the minimal exposure.

Safety:

The assessment scores of purpura, edema, erythema, hyperpigmentation, hypopigmentation, blistering and scaring from all post-treatments evaluation will be tabulated. The pain assessment scores obtained immediately post treatment will be tabulated. The mean scores for each side effect at each post treatment evaluation will be calculated.

Results:

Detailed results concerning the 2 subjects are shown in Table 2.

Herein, the SPF-like protection factor was from 8 to 15. As anticipated, less redness would be seen for each tested MED on the photoprotected side, when compared to unprotected control anterior forearm testing areas. Les pain was also felt on the photoprotected forearm when performing MED testing for equivalent dose when compared to the unprotected forearm.

After UV radiation exposure all immediate skin responses were recorded through observation, and photographs.

These included several types of typical responses such as the following: an immediate darkening or tanning, typically greyish or purplish in color, fading in 30 to 60 minutes, and attributed to photo-oxidation of existing melanin granules; immediate reddening, fading rapidly, and viewed as a normal response of capillaries and venules to heat, visible and infrared radiation; and an immediate generalized heat response, resembling prickly heat rash, fading in 30 to 60 minutes, and apparently caused by heat and moisture generally irritating to the skin's surface. After the immediate responses were noted, each subject shielded the exposed area from further UV radiation or light for the remainder of the test day. The MED was determined 22 to 24 hours after exposure.

Clinical results clearly confirmed the photoprotective effects of non-thermal pulsed 660 nm light therapy: erythema reduction was significant for both female participants. Briefly, for both participants, erythema followed MED testing on the photoprotected forearm, right after treatment. For the 32 year-old participant, redness clearly established after 6 hours, maximum peaking at hours and was maintained at 24 hours, indicating a SPF-like protection of at least 8. The 47 year-old woman had an important redness immediately after MED testing, however redness was about 60% less on the protected forearm. Erythema established quickly and peaked at 8 hours post UV exposure, and maintain at 24 h hours. A SPF-like photoprotection of 15 was granted for the 660 nm LumiPhase-R light. Participants increased the time they could spend under the UV lamp before developing erythema and reaching their MED, when compared to unprotected forearm. UV doses inducing redness could not lead to a similar response on the protected arm: erythema was clearly delayed right after UV exposure and at 24 hours, it was obvious non-thermal 660 nm light had granted a photoprotection by a factor of 8 and 15 respectively for the 32 and 47 year-old participants. For both subjects, pain during MED testing was a lot less intense (about 50%) for the anterior forearm previously treated with 660 nm light, for similar MED experimented on the anterior forearm when performing MED determination.

Discussion

The following beneficial effects were observed:

Pain and burning sensation during UV exposure was less intense for all treated anterior forearm, when compared to the control (unprotected anterior forearm).

Erythema immediately post UV exposure was reduced on the protected side.

Erythema and redness 5 hours post UV exposure was reduced on the protected side.

More UV-B intensity was required to achieved 1 MED on skin that was irradiated with the protecting radiation, underlying and SPF-like sun protection index provided by non-thermal 660 nm pulsed light treatments.

Therefore, the above-described experiments illustrate the claimed novel method for protecting mammalian skin against damages caused by a damaging radiation. Additionally, while only a limited set of parameters for the protective radiation was tested, the relatively large SPF-like results obtained suggest that a relatively large range of parameters is likely to produce similar effects.

Although the present invention has been described hereinabove by way of preferred embodiments thereof, it can be modified, without departing from the spirit and nature of the subject invention as defined in the appended claim.

References

1: Tsukahara K, Moriwaki S, Hotta M, Fujimura T, Sugiyama-Nakagiri Y, Sugawara S, Kitahara T, Takema Y. The effect of sunscreen on skin elastase activity in duced by ultraviolet-A irradiation. Biol Phanterior forearm Bull. 2005 December;28(12):2302-7.

2: Moon H I, Kwak J H, Zee O P, Chung J H. Regulation effect of 2',4',7-trihydroxyisoflavone on the expression of matrix metalloproteinase-1, 2 in ultraviolet-B irradiated primary cultured old aged human skin fibroblasts. Biol Phanterior forearm Bull. 2005 November;28(11):2173-5.

3: Xia J, Song X, Bi Z, Chu W, Wan Y. UV-induced NF-kappaB activation and expression of IL-6 is attenuated by (−)-epigallocatechin-3-gallate in cultured human keratinocytes in vitro. Int J Mol Med. 2005 November; 16(5):943-50.

4: Baumann L. How to prevent photoaging? J Invest Dermatol. 2005 October;125(4):xii-xiii. No abstract available.

5: Stratigos A J, Katsambas A D. The role of topical retinoids in the treatment of photoaging. Drugs. 2005;65(8):1061-72. Review.

6: Han K H, Choi H R, Won C H, Chung J H, Cho K H, Eun H C, Kim K H. Alteration of the TGF-beta/SMAD pathway in intrinsically and UV-induced skin aging. Mech Ageing Dev. 2005 May;126(5):560-7. Epub 2004 Dec. 23.

7: Fisher G J. The pathophysiology of photoaging of the skin. Cutis. 2005 February;75(2 Suppl):5-8; discussion 8-9. Review.

8: Moon H I, Lee J, Eun H C, Kim K H, Chung J H. The effect of tiarellic acid on the expressions of matrix metalloproteinase-1 and type 1 procollagen in ultraviolet irradiated cultured human skin fibroblasts. J Ethnophanterior forearmacol. 2005 Apr. 8;98(1-2): 185-9.

9: Nishigori C, Haltori Y, Arima Y, Miyachi Y. Photoaging and oxidative stress. Exp Dermatol. 2003;12 Suppl 2:18-21.

10: Maier T, Korting H C. Sunscreens—which and what for? Skin Phanterior forearmacol Physiol. 2005 November-December;18(6):253-62. Epub 2005 Aug 19. Review.

11: Loser K, Scherer A, Krummen M B, Varga G, Higuchi T, Schwarz T, Sharpe A H, Grabbe S, Bluestone J A, Beissert S. An important role of CD80/CD86-CTLA4 signaling during photocarcinogenesis in mice. J Immunol. 2005 May 1;174(9):5298-305.

12: Afaq F, Adhami V M, Mukhtar H. Photochemoprevention of ultraviolet B signaling and photocarcinogenesis. Mutat Res. 2005 Apr 1;571(1-2):153-73. Epub 2005 Jan. 23. Review.

13: Agar N, Young A R. Melanogenesis: a photoprotective response to DNA damage? Mutat Res. 2005 Apr. 1;571(1-2): 121-32. Epub 2005 Jan. 23. Review.

14: Melnikova V O, Ananthaswamy H N. Cellular and molecular events leading to the development of skin cancer. Mutat Res. 2005 Apr. 1;571(1-2):91-106. Review.

15: Chen P H, Lan C C, Chiou M H, Hsieh M C, Chen G S. Effects of arsenic and UVB on normal human cultured keratinocytes: impact on apoptosis and implication on photocarcinogenesis. Chem Res Toxicol. 2005 February; 18(2): 139-44.

16: Hussein M R. Ultraviolet radiation and skin cancer: molecular mechanisms. J Cutan Pathol. 2005 Mar;32(3):191-205. Review.

17: Wang L E, Xiong P, Strom S S, Goldberg L H, Lee J E, Ross M I, Mansfield P F, Gershenwald J E, Prieto V G, Cormier J N, Duvic M, Clayman G L, Weber R S, Lippman S M, Amos Cl, Spitz M R, Wei Q. In vitro sensitivity to ultraviolet B light and skin cancer risk: a case-control analysis. J Natl Cancer Inst. 2005 Dec. 21;97(24):1822-31.

18: Menezes S, Coulomb B, Lebreton C, Dubertret L. Non-coherent near infrared radiation protects normal human dermal fibroblasts from solar ultraviolet toxicity. J Invest Dermatol. 1998 October;111 (4)-:629-33.

19: Schieke S, Stege H, Kurten V, Grether-Beck S, Sies H, Krutmann J. Infrared-A radiation-induced matrix metalloproteinase 1 expression is mediated through extracellular signal-regulated kinase Y2 activation in human dermal fibroblasts. J Invest Dermatol. 2002 December;119(6):1323-9.

20: Kim H H, Lee M J, Lee S R, Kim K H, Cho K H, Eun H C, Chung J H. Augmentation of UV-induced skin wrinkling by infrared irradiation in hairless mice. Mech Ageing Dev. 2005 November;126(11):1170-7.

21: Schieke S M, Schroeder P, Krutmann J. Coetaneous effects of infrared radiation: from clinical observations to molecular response mechanisms. Photodermatol Photoimmunol Photomed. 2003 October; 19(5):228-34. Review.

22: Halper J, Griffin A, Hu W, Jung C, Zhang J, Pan H, Kisaalita W S, Foutz T L, Frazier K S. In vitro culture decreases the expression of TGF(beta), Hsp47 and type I procollagen and increases the expression of CTGF in avian tendon explants. J Musculoskelet Neuronal Interact. 2005 March;5(1):53-63.

23: Barolet D, Boucher A, Bjerring P. In vivo human dermal collagen production following LED-based therapy: The importance of treatment parameters. 25th Anniversary Meeting of the American Society for Laser Medicine and Surgery, March 30-Apr. 3, 2005. Poster session (259).

24: Marionnet C, Bernerd F, Dumas A, Verrecchia F, Mollier K, Compan D, Bernard B, Lahfa M, Leclaire J, Medaisko C, Mehul B, Seite S, Mauviel A, Dubertret L. Modulation of gene expression induced in human epidermis by environmental stress in vivo. J Invest Dermatol. 2003 December; 121(6): 1447-58.

25: Morliere P, Moysan A, Gaboriau F, Santus R, Maziere J C, Dubertret L. [Ultraviolet A radiation and the skin. Implications of activated forms of oxygen. Current trends and newest results] Pathol Biol (Paris). 1992 February;40(2):160-8. Review. French.

26: Frank S, Oliver L, Lebreton-De Coster C, Moreau C, Lecabellec M T, Michel L, Vallette F M, Dubertret L, Coulomb B. Infrared radiation affects the mitochondrial pathway of apoptosis in human fibroblasts. J Invest Dermatol. 2004 November; 123(5):823-31.

27: Djavaheri-Mergny M, Javelaud D, Wietzerbin J, Besancon F. NF-kappaB activation prevents apoptotic oxidative stress via an increase of both thioredoxin and MnSOD levels in TNFalpha-treated Ewing sarcoma cells. FEBS Lett. 2004 Dec. 3;578 (1-2):111-5. J Invest Dermatol. 2004 November;123(5):823-31.

TABLE 1

Characteristics of study participants for experiments illustrating the use of 660 nm radiation pulse trains in preventing subsequent UV damage.

| 32 year-old Female | 47 year-old Female |
|---|---|
| Phototype II | Phototype II |
| Total of 10 photoprotection (LumiPhase-R) treatments | Total of 3 photoprotection (LumiPhase-R) treatments |
| Control: left anterior forearm | Control: left anterior forearm |
| Test: right anterior forearm | Test: right anterior forearm |
| 2 set of 5 daily 660 nm photoprotection (LumiPhase-R) treatments, performed 24 hours apart | Three 660 nm photoprotection (LumiPhase-R) treatments were spaced with 48 hours |

MED testing was performed on the last 660 nm photoprotection (LumiPhase-R) treatment day; on test anterior forearm-- MED determination had been previously determined on control anterior forearm 24 hours ahead.

TABLE 2

Experimental parameters and results of experiments illustrating the use of 660 nm radiation pulse trains in preventing subsequent UV damage for the patients of Table 1,

| | 1<br>32 year-old<br>Female | 2<br>47 year-old<br>Female |
|---|---|---|
| Fitzpatrick skin Phototype | II | II |
| Total number of 660 nm photoprotection (LumiPhase-R) treatments | 10 | 3 |
| How were 660 nm photoprotection (LumiPhase-R) treatments delivered: | 2 set of 5 daily 660 nm photoprotection (LumiPhase-R) treatments, performed 24 hours apart, two weeks prior UV exposure | 660 nm photoprotection (LumiPhase-R) treatments were spaced with 48 hours, in the week prior to UV exposure |
| Skin redness immediately post UV exposure, versus control anterior forearm, for corresponding MEDs: | 30% reduction | 60% reduction |
| Skin redness at 5 hours post UV exposure, versus control anterior forearm, for corresponding MEDs: | 40% reduction | 50% reduction |
| Skin redness at 24 hours post UV exposure, versus control anterior forearm, for corresponding MEDs: | 40% reduction | 60% reduction |
| SPF-like value granted by 660 nm photoprotection (LumiPhase-R) treatments prior to UV exposure. | 8 (possibly up to 15) | 15 (possibly up to 20) |

What is claimed is:

1. A method for protecting in vivo human skin against photodamage caused by an exposure to a damaging radiation including ultraviolet radiation, said method comprising:
irradiating the human skin before the exposure to the damaging radiation with a protective radiation, the protective radiation including radiation having a wavelength larger than the wavelength of the damaging radiation, the protective radiation including non-coherent light having a bandwidth of from about 10 nm to about 50 nm, the protective radiation being irradiated onto the human skin under conditions suitable for reducing photodamage to the human skin caused by the damaging radiation;

said irradiation of the human skin before the exposure to the damaging radiation with a protective radiation including irradiating the human skin with a first pulse having a power density between 20 and 100 mW/cm$^2$;

irradiating the human skin with a second pulse;

emitting the first pulse for a duration of about 100 microseconds to about 5 milliseconds; and separating the first pulse from the second pulse by an inter-pulse interval of about 1 microsecond to about 1 millisecond;

the protective radiation including at least two pulse trains, each pulse train including the first pulse and the second pulse, the irradiation of the human skin before the exposure to the damaging radiation with a protective radiation further including emitting a first pulse train; and separating the first pulse train from a second pulse train by an inter-pulse train interval of about 500 microseconds to about 2.25 millisecond;

wherein the inter-pulse train interval is greater than the inter-pulse interval; and wherein said irradiation of the human skin is performed under non-thermal and non-ablative conditions in which temperature of said human skin remains below a predetermined overheating temperature, said predetermined overeating temperature being about 5° C. above a maximal non-pathological in-vivo human skin temperature;

said method further comprising exposing the human skin to the damaging radiation after irradiating the human skin with the protective radiation;

whereby irradiation of the human skin before the exposure to the damaging radiation with the protective radiation reduces damages to the human skin caused by the damaging radiation as compared to human skin that was not subject to irradiation with the protective radiation.

2. A method as defined in claim 1, wherein the damaging radiation includes radiation intended to treat a medical condition, the protective radiation reducing side effects of the damaging radiations while allowing the treatment of the medical condition to occur.

3. A method as defined in claim 1, wherein the inter-pulse interval is from about 100 microseconds to about 0.5 milliseconds.

4. A method as defined in claim 1, wherein a ratio of the duration divided by the inter-pulse interval is one of about 0.1 to about 10 and about 0.5 to about 2.

5. A method as defined in claim 1, wherein the total fluence of the protective radiation is from about 2 J/cm$^2$ to about 10 J/cm$^2$.

6. A method as defined in claim 1, further comprising cooling the human skin so as to maintain the human skin irradiated at a temperature below said predetermined overheating temperature.

7. A method as defined in claim 1, wherein a ratio of the inter-pulse train interval to the inter-pulse interval is from about 2 to about 10.

8. A method as defined in claim 1, wherein a number of pulses within each pulse train is from about 2 to about 100 pulses.

9. A method as defined in claim 8, wherein a number of pulses within each pulse train is from about 3 to about 10 pulses.

10. A method as defined in claim 1, further comprising the steps of:

irradiating the human skin over at least two treatments wherein a treatment includes at least one pulse train;

providing an inter-treatment time interval between treatments, the inter-treatment time interval being from about 12 hours to about 4 days.

11. A method as defined in claim 10, wherein said irradiation of the human skin includes irradiating the human skin over between 2 and 10 treatments, the treatments each including one or more pulse trains.

12. A method as defined in claim 5, wherein:

each pulse train includes from about 4 to about 10 pulses;

the pulses within each pulse train last from about 250 microseconds to about 1 millsecond;

the inter-pulse interval is from about 100 microseconds to about 0.5 millisecond;

the inter-pulse train interval is from about 500 microseconds to about 1 second; and the total fluence is between 2 and 6 J.

13. A method as defined in claim 12, wherein each pulse train includes about 4 pulses of radiation having a central wavelength of about 660 nm;

the pulses within each pulse train lasting about 500 microseconds;

the inter-pulse interval is about 150 microseconds;

the inter-pulse train interval is about 1.55 milliseconds;

the irradiance is about 50 m W/cm$^2$;

the total fluence is about 4 J.

* * * * *